United States Patent [19]

Rabinovitz et al.

[11] Patent Number: 5,124,351
[45] Date of Patent: Jun. 23, 1992

[54] PHARMACEUTICAL COMPOSITIONS FOR THE TREATMENT OF CANCERS SUSCEPTIBLE TO TREATMENT WITH THE COPPER COMPLEX OF S-(METHYLTHIO)-DL-HOMOCYSTEINE OR THE L-ENANTIMORPH THEREOF

[75] Inventors: Marco Rabinovitz; Joyce M. Fisher, both of Bethesda, Md.

[73] Assignee: The United States of America as represented by the Secretary of the Department of Health and Human Services, Washington, D.C.

[21] Appl. No.: 315,911

[22] Filed: Feb. 27, 1989

[51] Int. Cl.⁵ .................. A61K 31/30; A61K 31/195
[52] U.S. Cl. .................................. 514/499; 514/500; 514/562
[58] Field of Search .................. 514/499, 500, 562

[56] References Cited

PUBLICATIONS

Rabinovitz et al, Proceedings of AARC, vol. 29, p. 325, Abstract 1293, 1988.

*Primary Examiner*—Jerome D. Goldberg
*Attorney, Agent, or Firm*—Birch, Stewart, Kolasch & Birch

[57] ABSTRACT

An injectable pharmaceutical composition for the treatment of cancers susceptible to treatment therewith, the composition comprising:
  (a) an effective amount of S-(methylthio)-DL-homocysteine or the L-enantimorph thereof;
  (b) an effective amount of a copper chelate of nitrilotriacetic acid or an effective amount of a copper chelate of a bis-thiosemicarbazone; and
  (c) a pharmaceutically acceptable carrier.

2 Claims, 9 Drawing Sheets

PHARMACEUTICAL COMPOSITIONS FOR THE TREATMENT OF CANCERS SUSCEPTIBLE TO TREATMENT WITH THE COPPER COMPLEX OF S-(METHYLTHIO)-DL-HOMOCYSTEINE OR THE L-ENANTIMORPH THEREOF

FIELD OF THE INVENTION

The present invention broadly relates to the treatment of cancers in a patient, wherein such cancers are susceptible to treatment by co-administering to the patient S-(methylthio)-DL-homocysteine and a copper delivery agent.

BACKGROUND OF THE INVENTION

S-(Methylthio)-homocysteine (SMETH) is disclosed in Japanese Patent Publication Kokai No. 77 83710, Jul. 12, 1977 (C.A. 88:23393m). This publication, however, fails to recognize the potential therapeutic effects of SMETH, particularly its ability to function as a potent glutamine antagonist in cancer cells. Other glutamine antagonists which are effective as anti-cancer agents are natural antibiotics. These particularly include 6-diazo-5-oxo-norleucine, azaserine, and acivicin. These antibiotic compounds tend to be disadvantageous because they exhibit a low degree of biochemical specificity.

SUMMARY OF THE INVENTION

It is an object of the present invention to provide a pharmaceutical composition for the treatment of cancers susceptible to treatment therewith in animals and humans in a non-toxic manner.

Another object of the present invention is to provide an effective anti-cancer agent for treating cancers susceptible to treatment therewith, and a method for its delivery, which anti-cancer agent will function as a glutamine antagonist.

Yet another object of the present invention is to provide such an anti-cancer agent and method for its delivery, so that the same agent will exhibit a high degree of biochemical specificity.

Still another object of the present invention is to treat cancers susceptible to treatment with the pharmaceutical compositions herein provided based upon a new principle of binary cytotoxicity to tumor cells.

These and other objects are accomplished by providing a pharmaceutical composition for the treatment of cancers susceptible to treatment therewith, the composition comprising co-administering to a human or animal with a cancer susceptible to treatment (a) S-(methylthio)-DL-homocysteine (SMETH) or the L-enantiomorph; and (b) copper ion sequestered in a chelate functioning as a delivery agent for copper, in which an anti-cancer agent is formed by a complex of (a) and the copper of (b).

The present pharmaceutical compositions may be effective in treating many types of cancers susceptible to treatment therewith, including the treatment of ovarian cancer which has spread within the peritoneum.

The S-(methylthio)-DL-homocysteine can be utilized in its racemic form, or the L stereo isomeric form The copper delivery agent can vary, and this agent delivers the copper as a non-toxic chelate. The copper can be delivered as a copper chelate of bis-thiosemicarbazones. More preferably, the copper is delivered as a non-toxic chelate of nitrilotriacetic acid (which is known to be effective as a copper delivery agent in humans).

The S-(methylthio)-DL-homocysteine (or its L-stereo isomeric form) and copper delivery agent can be administered intraveneously and intraparentally. The S-(methylthio)-DL-homocysteine (or its L-stereo isomeric form) and copper delivery agent can be administered, for example, as a saline solution, but the solution cannot contain sulphites or ascorbic acid, or other similar reducing agents.

The S-(methylthio)-DL-homocysteine (or its L-stereo isomeric form) compound can be administered at a concentration of 0.001 to 0.02M without any material toxicity. The copper can also be administered, via its delivery agent, to a concentration of up to 0.02M without any material toxicity.

The components (a) and (b) may be administered to a patient as a mixture or independently. If components (a) and (b) are administered independently, they may be administered substantially simultaneously or one component may be administered before the other. The timing of the administration of ,a) and (b) should be such that components (a) and (b) simultaneously achieve affective levels in body tissues for forming an effective amount of a complex of (a) and the copper of (b) in cancer cells which are susceptible to treatment therewith.

BRIEF DESCRIPTION OF THE DRAWINGS

The present invention will become more fully understood from the detailed description given hereinbelow and the accompanying drawings which are given by way of illustration only, and thus are not limitative of the present invention, wherein:

FIGS. 9A and 9B present a diagrammatic representation of glutamine, and copper - SMETH at the enzyme reactive site, in which:

FIG. 9A denotes glutamine

FIG. 9B denotes copper - SMETH.

DETAILED DESCRIPTION OF THE INVENTION

S-(methylthio)-homocysteine, (SMETH), was prepared to investigate its role as a pro-drug for delivery of homocysteine to cells. It was modeled after the lower homolog, S-(methylthio)-cysteine. (See Rabinovitz, M., and Johnson, J. M. "Synthesis of 4-thiamethionine and Its Effect on Energy Metabolism and Amino Acid Incorporation into Protein of Ehrlich Ascites Tumor Cells," *Biochem. Pharmacol.* 7: 100–108 (1961)), which upon intracellular reduction of the disulfide bond delivered cysteine to cells. (See Mohindru, A., Fisher, J. M., and Rabinovitz, M. 'Oxidative Damage' To A Lymphoma In Primary Culture Under Aerobic Conditions Is Due Solely To A Nutritional Deficiency Of Cysteine", *Proc. Am. Assoc. Cancer Res.*, 24:1 (1983); and Pierson, H. F., Fisher, J. M., and Rabinovitz, M., "Depletion of Extracellular Cysteine With Hydroxocobalamine And Ascorbate In Experimental Murine Cancer Chemotherapy," *Cancer Res.* 45:4727–4731 (1981)). Similar delivery of homocysteine would promote the formation of S-adenosylhomocysteine, a potent inhibitor of cellular methylations (See Ueland, P. M., "Pharmacological and Biochemical Aspects of S-adenosylhomocysteine and S-adenosylhomocysteine Hydrolase," *Pharmacol. Rev.* 34:223–253 (1982)) and projected end product for chemotherapy (See Borchart, R. T. "S-Adenosyl-L-methionine-dependent Macromolecule Methyl-transferases: Potential Targets For The Design of Chemotherapeutic Agents," *J. Med. Chem.* 23:347–357 (1981)). Although SMETH was found to be a potent inhibitor of cellular proliferation, it did not function by t e above anticipated mechanism.

PREPARATION OF SMETH

S-(Methylthio)-DL-homocysteine (DL-SMETH) was prepared from DL-homocysteine (Research Organics, Inc., Cleveland, OH) and methyl methanethiolsulfonate (Fairfield Chem. Co., Blythewood, S.C.) by a modification for the methylthiolation of L-cysteine as described by Smith et al. (Smith, D. J., Maggio, E. I., and Kenyon, G. L. "Simple Alkanethiol Groups For Temporary Blocking Of Sulfydryl Groups Of Enzymes," *Biochemistry* 14:766-771 (1975)). The L-enantiomorph, L-SMETH, was prepared following reduction of L-homocysteine (Sigma Chem. Co., St. Louis, MO) with sodium in liquid ammonia. The excess sodium was removed by the addition of ammonium chloride and the ammonia evaporated at room temperature under nitrogen. The residue was dissolved in oxygen free water and the solution neutralized to pH 6.5–7.0 with hydrochloric acid. A 1.25 molar excess of methyl methanethiolsulfonate in ethanol was added slowly and the product crystallized after 2 hours in an ice bath. The crystals were washed with ethanol and peroxide-free ether and dried over phosphorus pentoxide. An analysis was conducted (performed by Atlantic Microlab. Inc., Atlanta, GA) for SMETH, calculated, C, 33.13; H, 6.12; N,7.73; S, 35.37; Similarly found, for DL-SMETH, C, 33.21; H, 6.12; N, 7.71; S, 35.28; for L-SMETH C, 33.19; H, 6.12; N, 7.68; S, 35.3(. The racemate was resolved into two peaks and the chiral purity of L-SMETH was determined to be at least 99.9 per cent by column chromatography with a resolving column.

GROWTH AND ITS INHIBITION IN CELL CULTURE

An L1210 established murine leukemia line was maintained in RPMI 1630 medium (Quality Biologicals, Gaithersburg, MD) containing 16.5% fetal bovine serum (Advanced Biotechnologies, Silver Spring, Md.) and Gentamycin (Schering Corp., Kenilworth, NJ) 40 µg/ml. Cytotoxicity of SMETH was assessed as follows. Cells were harvested at mid-log phase ($8-10 \times 10^5$ cells/ml) washed with fresh growth medium and resuspended at $1 \times 10^5$ cells per ml as determined by a model ZBI Coulter Counter (Coulter Electronics, Hialeah, Fla.). Suspensions (7 ml) were added to 25 cm² Corning flasks, and SMETH. 20 mM in water, with or without copper sulfate, 2 mM in water were added as dilutions in water at no greater than 10 µl/ml of the cell suspension.

Cells were grown at 37° C. for designated times in tightly stoppered flasks and cell density was determined as indicated above. Cell volume distribution was monitored with a C1000 Channelyzer with standard size latex particles (Coulter) as reference. The results are expressed as growth fraction (N—No/No) or as percent growth fraction compared to appropriate controls.

ANALYSIS OF NUCLEOSIDE TRIPHOSPHATE POOLS

For analytical studies the total incubation volume was increased to 100 ml in 175 cm² flasks, with the same proportions of cells and solutions described for the smaller incubation volumes. At the appropriate time, growth was terminated by shaking the flasks in ice and all further steps were performed with ice-cold reagents and under refrigerated conditions. On reaching 4° C., the cells were pelleted in a refrigerated centrifuge and extracted with 500 µl of 10% TCA. The precipitate was sedimented in a microcentrifuge tube, the supernatant fluid transferred to another such tube and extracted vigorously with an equal volume of freon (1,1,2-trichloro-1,2,2.-trifluoroethane) containing tri-n-octylamine in 4:1 proportions by volume as described by Khym (See Khym, J. X. "An Analytical System For Rapid Separation Of Tissue Nucleotides At Low Pressures On Conventional Anion Exchangers", *Clin. Chem.* 21:1245 –1252 (1975)). The supernatant fluid was removed and 200 µl analyzed by HPLC with the use of a Whatman 5SAX column (12.5×0.4 cm) and ammonium phosphate, pH 3.5, gradient 0.02 m to 0.7 m) over 40 minutes. The detection of components was made by UV absorbance at 254 nm.

FLOW CYTOMETRIC ANALYSIS

Following an incubation, cells were fixed and stained as described by Crissman et al. (See Crissman, H. A., Van Egmond, J., Holdrinet, R. S., Pennings, A. and Haanen, C.,"Simplified Method For DNA And Protein Staining Of Human Hematopoietic Cell Samples", *Cytometry* 2:59-62 (1981)). Samples were analyzed on a Becton -Dickinson FACS 440 flow cytometer (Mountain View, CA). The argon -ion laser (Coherent Innova 90-5, Palo Alto, CA) was tuned to 488 nm and operated at a power output of 200 mw in the light stabilized mode. Fluorescein isothiocyanate fluorescence was determined with the use of a 535/15 band pass filter and propidium iodide fluorascence with a 630/22 band pass filter. Data from $2 \times 10^4$ cells were collected from each sample and anulyzed in a Becto -Dickinson Consort 40 computer system.

RESULTS AND DISCUSSION

SMETH Toxicity And Copper Potentiation

Figure 1:
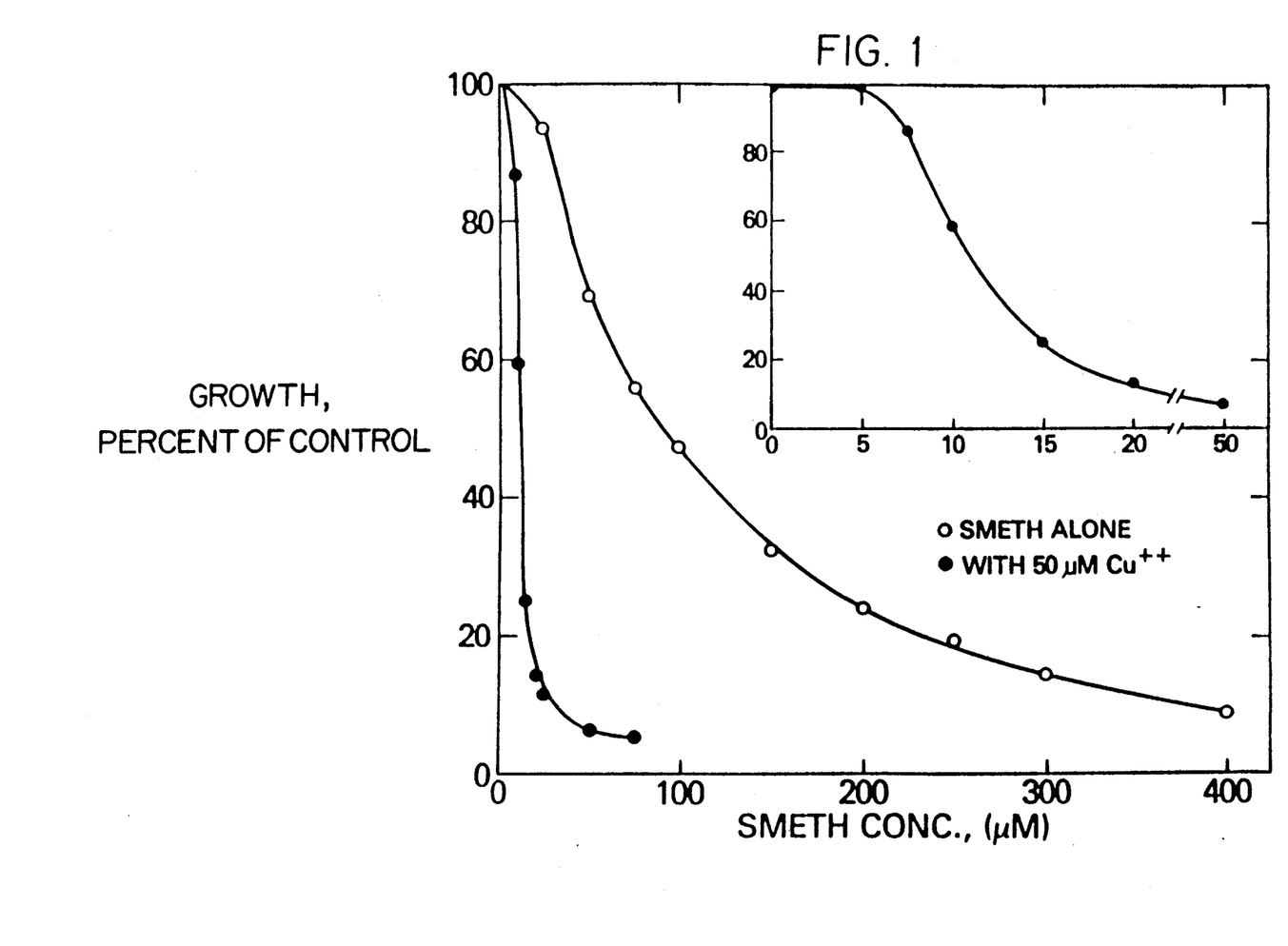
FIG. 1 shows the inhibition of growth of L1210 cells in culture by S-(methylthio)-DL-homocysteine (SMETH) and its potentiation by copper ion.
Figure 2:
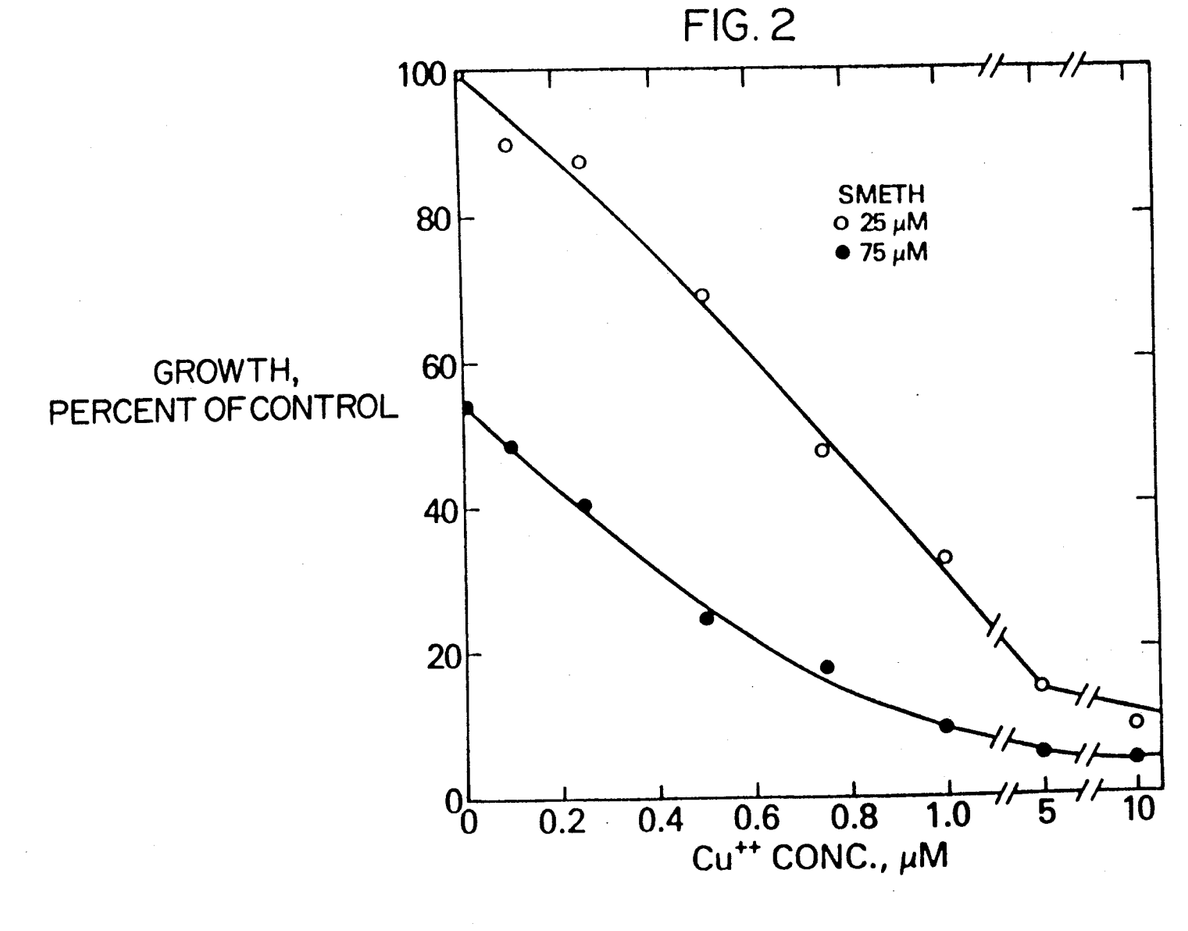
FIG. 2 illustrates the potentiation of the inhibitory activity of a threshold and $ID_{50}$ concentration of S-(methylthio) -DL-homocysteine by copper ion.
Figure 3:
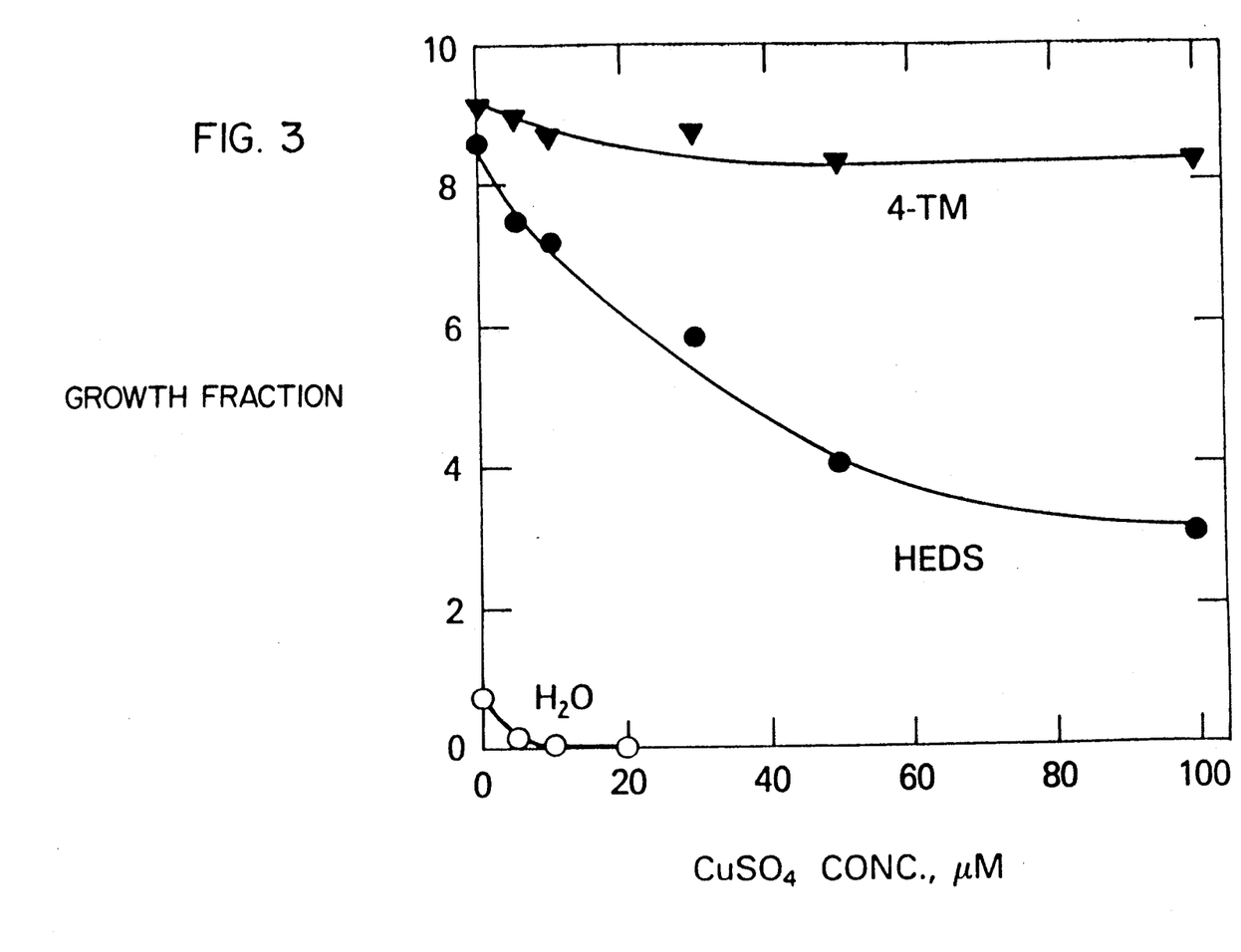
FIG. 3 shows that the lower homolog of SMETH protects L1210 cells in primary culture from copper induced toxicity.

SMETH was cytotoxic to L1210 cells in culture when present at a broad range of micromolar concentrations The range of inhibitory concentration was both reduced and narrowed in the presence of copper ion (FIG. 1), when the cells were also incubated for 40 hours. This ion was very effective at micromolar concentrations in bringing a threshold level of SMETH (25 μM) to a completely inhibitory concentration (FIG. 2), while being non-toxic itself at much higher levels. (The cells also were incubated for 40 hours). (See FIG. 3 of Mohindru, A., Fisher, J. M., and Rabinovitz, M. "2,9-Dimethyl-1,10-phenanthroline (neocuproine): A Potent, Copper-dependent Cytotoxin With Anti-tumor Activity.)" A concentration of 10 μM was more than adequate as a potentiating dose, but at this concentration other metal ions ($Zn^{++}$, $Mn^{++}$, $CO^{++}$, $Ni^{++}$, $Cr^{+++}$) were ineffective. Of interest is the fact that the lower homolog of SMETH, S-(methylthio)-L-cysteine or 4-thiamethionine is not cytotoxic in the presence of copper, and actually protected L1210 cells in primary culture from growth inhibition by copper (FIG. 3) due to depletion of cysteine (See Mohindru, A., Fisher, J. M., and Rabinovitz, M., "Endogenous Copper Is Cytotoxic To A Lymphoma In Primary Culture Which Requires Thiols For Growth", *Experientia* 41:1064–1066 (1985). To obtain the data for FIG. 3, the incubation was performed as in FIG. 2, except that the L1210 cells were obtained directly from the mouse (See Mohindru, A., Fisher, J. M., and Rabinovitz, M., "Endogenous Copper Is Cytotoxic To A Lymphoma In Primary Culture Which Requires Thiols For Growth", *Experientia* 41:1064–1066 (1985)). Such cells fail to grow unless supplemented with an appropriate mercaptan or disulfide (See curve o—o in FIG. 3). Hydroxyethyl Disulfide (HEDS), the oxidized form of mercaptoethanol, promoted growth, but this was inhibited by high copper concentrations (See curve —. in FIG. 3). S-(methylthio)-L-cysteine, also termed 4-thiamethionine (4TM), at a concentration of 50 μM, supported growth which was independent of copper ion concentration (See curve — in FIG. 3). Thus, both the organic and inorganic moieties of this invention show high specificity in this inhibition.

STEREOSPECIFICITY

Figure 4:
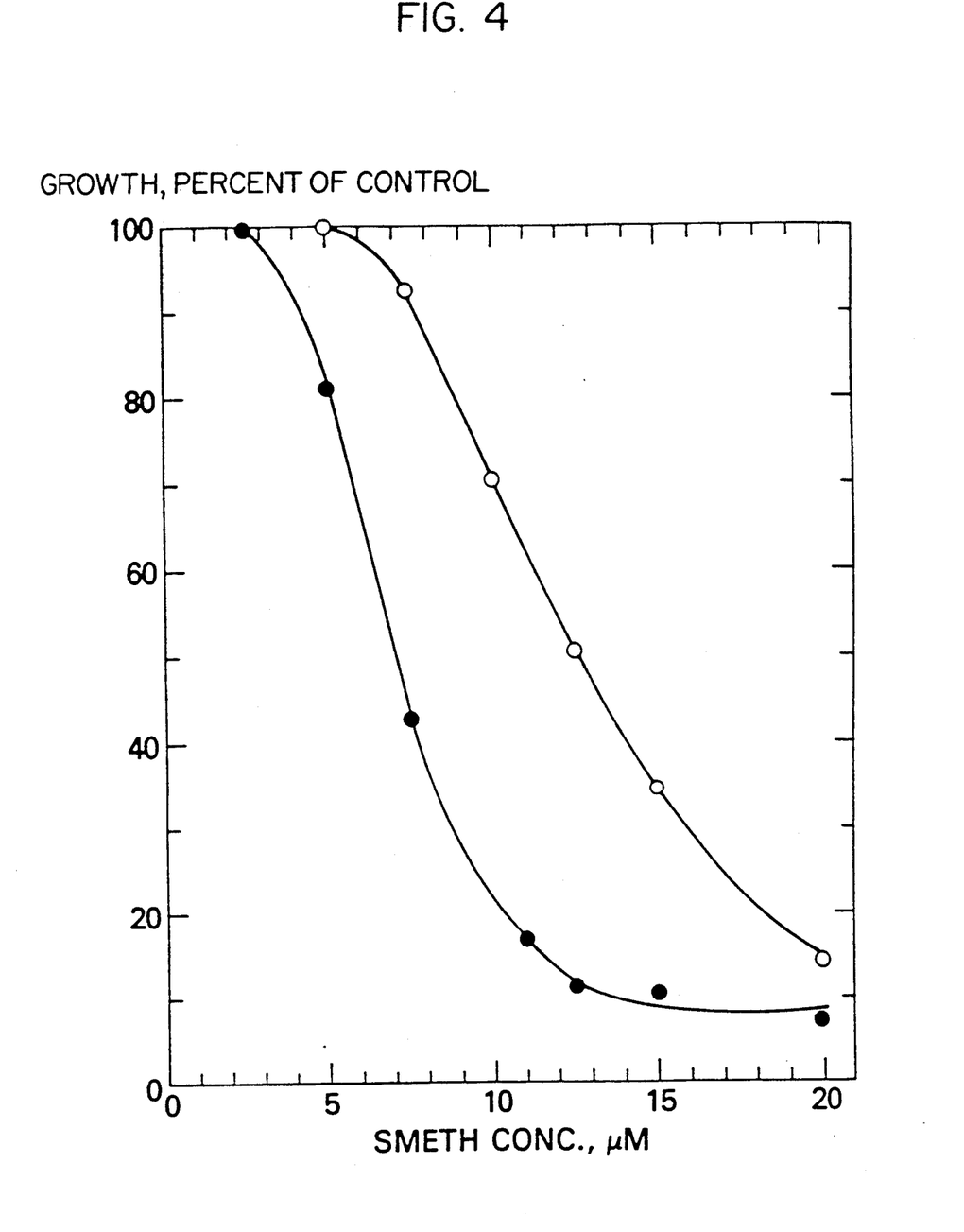
FIG. 4 shows that the cytotoxicity of S-(methylthio)-homocysteine is stereospecific.

The racemic form of SMETH was half as active as D-SMETH (FIG. 4). D-SMETH was completely inactive at 50 μM with 50 μM copper ion. The incubation was performed with copper ion at 50 μM as described in FIG. 1 with S-(methylthio)-DL-homocysteine DL-SMETH, (See curve o—o in FIG. 4) and with the pure L-enantiomorph, L-SMETH, (See curve — in FIG. 4). The use of 10 μM copper sulfate produced nearly identical results.

SMETH Toxicity Is Not Due To Homocysteine Delivery

Although SMETH was originally synthesized as a prodrug to deliver homocysteine to cells, inhibition analysis indicated that cytotoxicity was not due to this mechanism. Such toxicity has been reported for homocysteine thiolactone, which in combination with added adenosine and an adenosine deaminase inhibitor, such as deoxycoformycin, can block growth due to adenosyl-homocysteine formation (See Kredich, N. M., and Hershfield, M. S., "S-Adenosylhomo-cysteine Toxicity In Normal An Adenosine Kinase-deficient Lymphoblasts Of Human Origin", *Proc. Natl. Acad. Sci. U.S.A.* 76:2450–2454 (1979)). Adenosylhomocysteine is a potent inhibitor of cellular methylation processes and, as an endogenous product of methionine metabolism trapped intracellularly by added adenosine, is the reported basis for adenosine toxicity (See Kredich, N. M., and Martin Jr., D. W., "Role of S-adenosylhomocysteine in Adenosine-mediated Toxicity In Cultured Mouse T Lymphoma Cells", *Cell* 12:931–938 (1977)). The present inventors have evaluated this toxicity of adenosine across a concentration range for 5 to 40 μM. At 10 μM it was not toxic to L1210 cells, but it was toxic when added together with a non-toxic concentration of L-homocysteine thiolactone. Adenosine, however, did not increase the potency of a toxic dose of SMETH as shown in Table I. The failure of adenosine to promote SMETH toxicity suggested that such toxicity was not due to adenosylhomocysteine formation.

TABLE I

| Adenosine Does Not Potentiate SMETH Cytotoxicity | |
|---|---|
| | percent inhibition |
| L-Homocysteine Thiolactone 200 μM plus Adenosine 10 μM | 5 |
| Deoxycoformycin 20 μM | 39 |
| DL-SMETH 75 μm Plus Adenosine 10 μm Deoxycoformycin 20 μm | 46 |
| | 46 |

Percent inhibition is determined from the percent of growth fraction obtained with and without the compounds indicated.

Glutamine Protection Against SMETH Toxicity

Glutamine, at millimolar concentrations which supported growth, protected cells against SMETH and SMETH plug $Cu^{++}$ as shown in Table II.

TABLE II

| Glutamine Protects L1210 Cells from Growth Inhibition by SMETH and Copper-SMETH in a competitive manner. | | |
|---|---|---|
| Glutamine Conc. mM | L-SMETH 50 μM | L-SMETH 10 μM $Cu^{++}$, 10 μM |
| | growth (percent of control) | |
| 0.5 | 15 | 0 |
| 1.0 | 31 | 7.7 |
| 2.0 | 58 | 58 |
| 4.0 | 98 | 100 |

At these concentrations the full range for almost complete inhibition to complete protection is evident. This type of protection was not seen with other amino acids, some having a closer structural resemblance to SMETH. In fact, as can be seen in Table III, such amino acids promoted SMETH toxicity.

TABLE III

| Potentiation of Growth Inhibition by SMETH with Amino Acids | |
|---|---|
| | Conc.* for 50% further inhibition mM |
| L-Leucine | 1 |
| S-Ethyl-L-cysteine | 1 |
| DL-Isopropionine | 2 |
| L-Methionine | 2 |
| L-Norleucine | 2.5 |

*Estimated by interpolation. The DL-SMETH concentration was 75 or 100 μM.

This promotion of inhibitory activity may be due to the phenomenon termed "trans-stimulation of uptake" which is common in the amino acid series (See Schafer, J. A., and Jacquez, J. A., "Transport Of Amino Acids In Ehrlich Ascites Cells: Competitive Stimulation", *Biochim. Biophys. Acta* 135:741–750 (1967)). Such increased uptake would increase cytotoxicity. Further analysis of this problem would require radioactive material.

Amination Of Uridine To Cytidine As Site Of Inhibition

Figure 5:
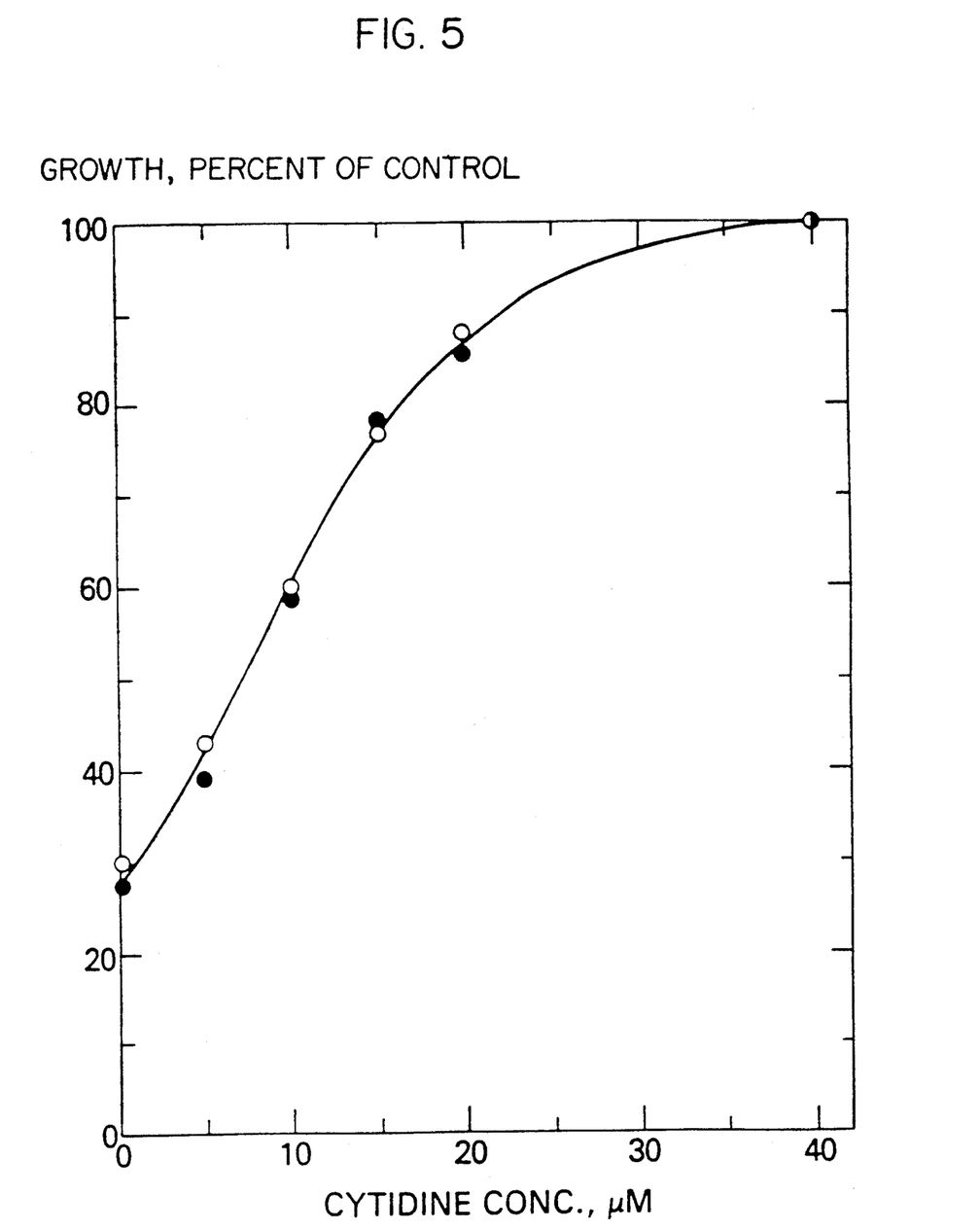
FIG. 5 illustrates that cytidine protects L1210 cells from the cytotoxicity of S-(methylthio)-L-homocysteine and copper ion.
Figure 6A:
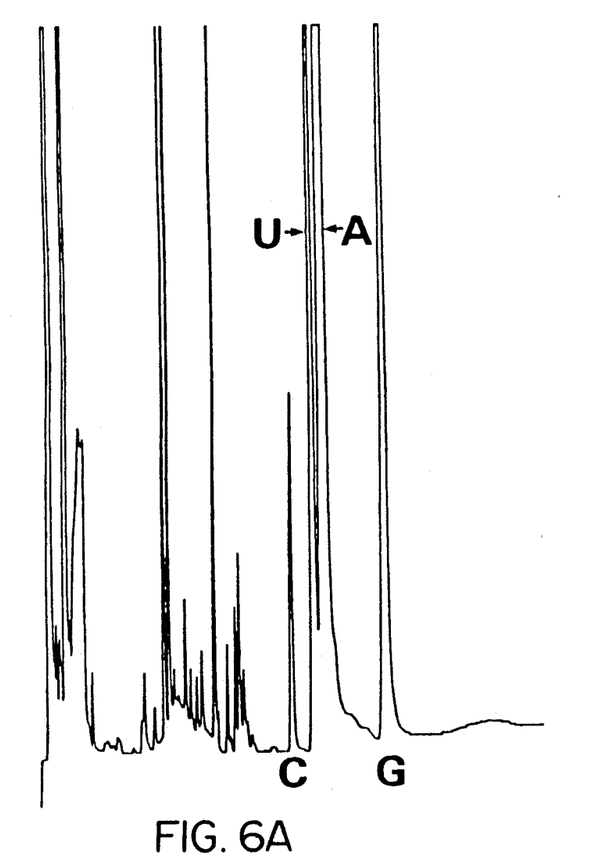
FIGS. 6A and 6B present the analysis of the nucleoside triphosphate content of cells incubated without (FIG. 6A) and with S-(methylthio)-L-homocysteine and copper ion (FIG. 6B)
Figure 6B:
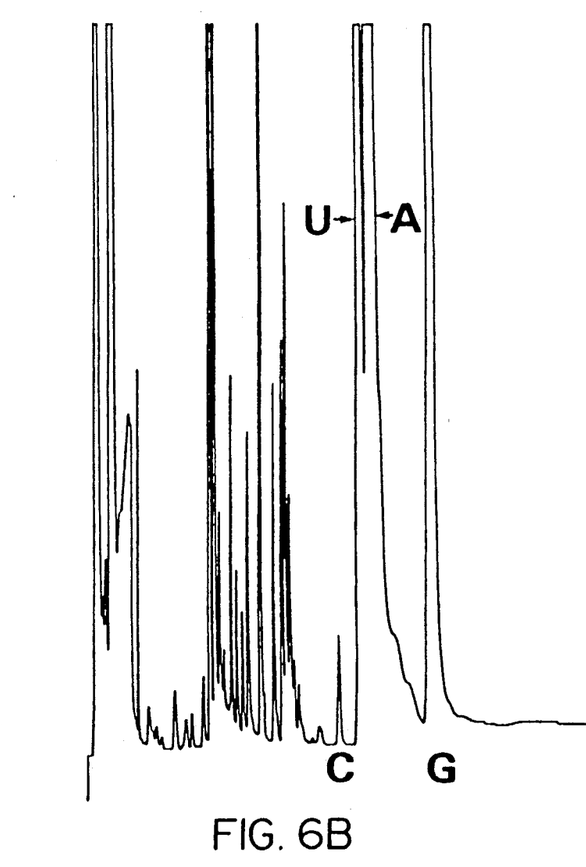

Among the several biochemical roles of glutamine, that involving the amination of uridine-5'-triphosphate (UTP) to cytidine-5'-triphosphate (CTP) was the only locus blocked by copper-SMETH. This conclusion was sustained by the following two observations: (1) Cytidine alone protected the cells from growth inhibition, and this protection was non-competitive, equivalent concentrations of cytidine being equally effective at two concentrations of copper-SMETH which gave maximal growth inhibition (See FIG. 5). (To obtain the data in FIG. 5, the cells were incubated with S-(methylthio)-L-homocysteine 15 µM, (curve ○—○) and 30 µM (curve — )together with their corresponding concentrations of copper sulfate). Uridine and guanosine were ineffective in such protection; and (2) HPLC analysis of cells inhibited in growth showed greater than a ⅓ diminution of CTP content but a two-fold elevation of UTP, ATP and GTP (See FIG. 6). To obtain the data in FIG. 6, the cells were incubated for 14 hours in the medium described in the above section entitled Growth And Its Inhibition In Cell Culture, but containing only 1 mM glutamine, ½ the normal concentration. The inhibited culture also contained 15 µM each of S-(methylthio)-L-homocysteine and copper sulfate. At the end of the incubation, the cell density in the inhibited culture was determined, and the entire population centrifuged for analysis. An aliquot containing an equal number of cells from the control culture was removed for comparison, and both samples processed and analyzed as described in the above section entitled Analysis of Nucleoside Triphosphate Pools. In FIG. 6A represents controls, and FIG. 6B represents inhibited culture. Letters with their corresponding peaks indicate the separated nucleotide triphosphate shown below, followed by retention times and the effect of copper-SMETH.

C, cytidine triphosphate; 20.0 min, decreased to 29% of control

U, uridine triphosphate; 21.3 min, increased to 233% of control

A, adenosine triphosphate; 22.6 min, increased to 196% of control

G, guanosine triphosphate; 27.5 min, increased to 186% of control

The modal volume of the control cells was (20 cubic microns and that of the inhibited cells 1140 cubic microns. Other uncharacterized peaks were also elevated in the inhibited sample. Such elevated levels of cellular constituents may be due to the increased volume of inhibited cells as described below.

Cell Expansion And Unbalanced Growth

Figure 7:
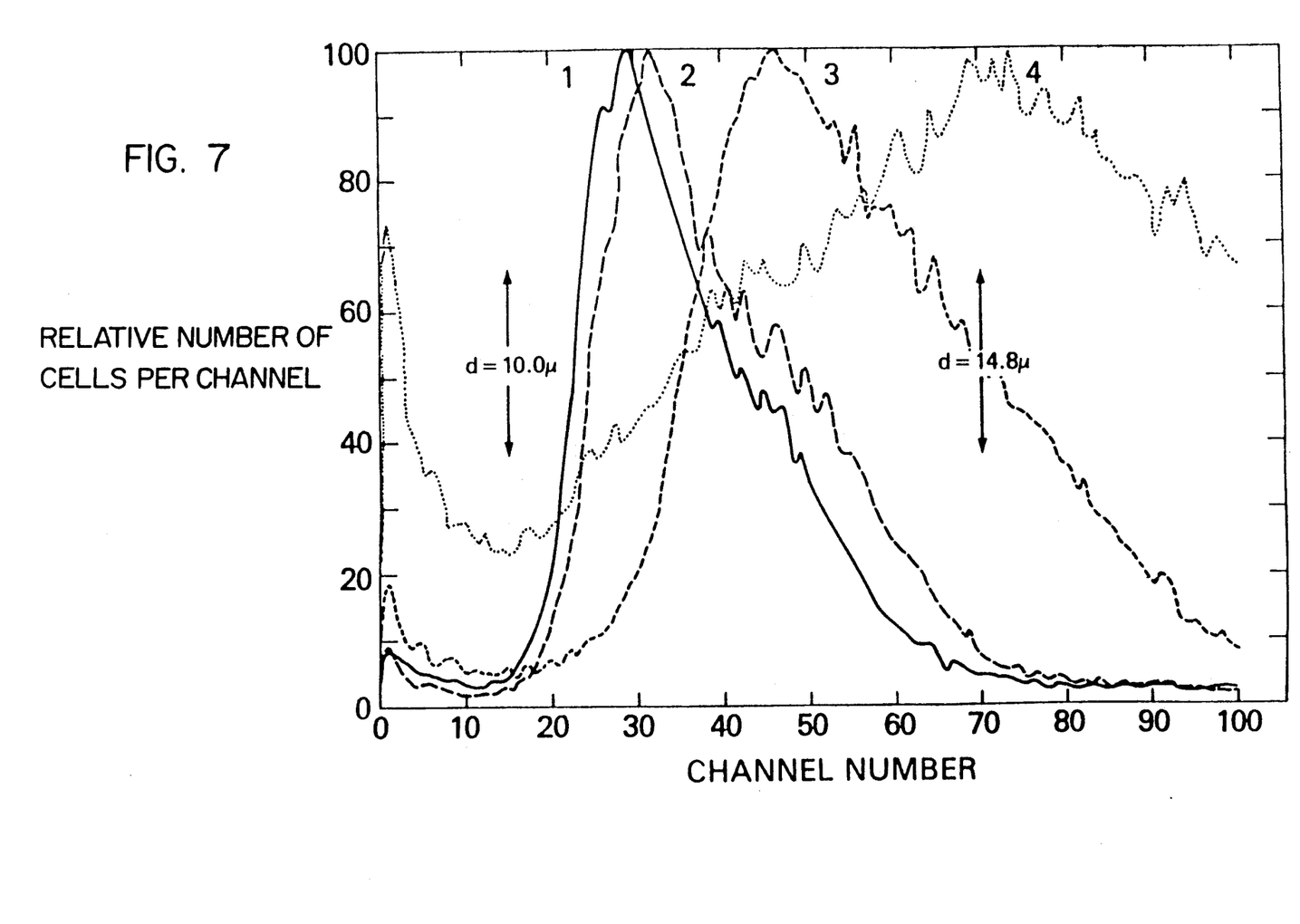
FIG. 7 shows the progression of volume increase and lysis of L1210 cells from inhibited cultures.
Figure 8:
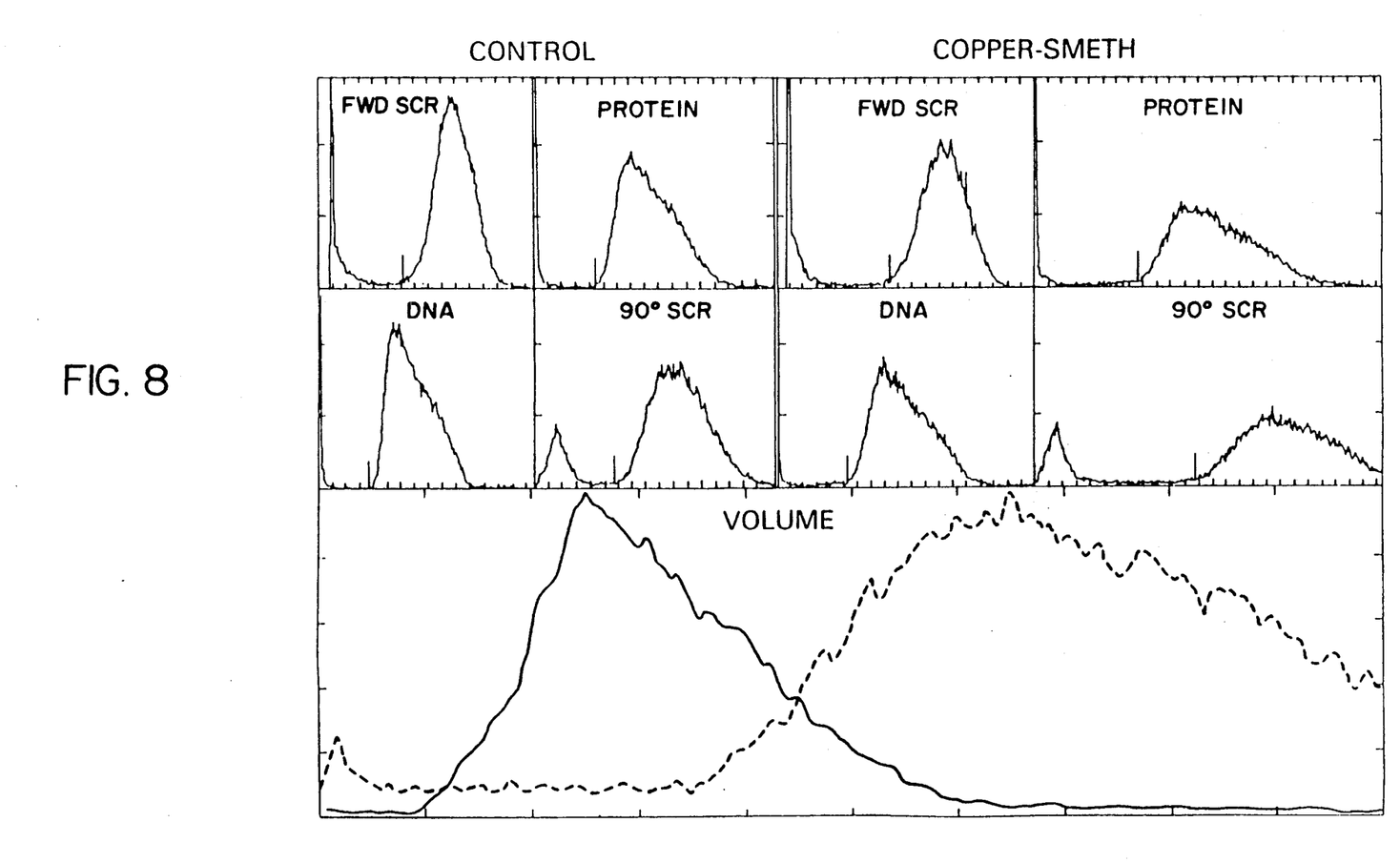
FIG. 8 illustrates the flow cytometric analysis of L1210 cells from cultures inhibited with S-(methylthio)-L-homocysteine and copper ion.

Characteristic of SMETH and copper-SMETH growth inhibition is the progressive increase in cell volume observed over a two day period (See FIG. 7). To obtain the data in FIG. 7, cells were incubated under standard conditions with S-(methylthio)-L -homocysteine and copper sulfate, each 15 µM, and cell volume monitored during the course of the incubation. Curve (1) denotes control cells, modal volume in cubic microns: 870; Curve (2) denotes cells with inhibitor for 16 hours, modal volume in cubic microns: 915; Curve (3) denotes cells with inhibitor for 24 hours, modal volume in cubic microns: 1270; and Curve (4) denotes cells with inhibitor for 40 hours, modal volume in cubic microns: 1820. Ultimately, the cells burst, as indicated by the accumulation of debris shown near the ordinate. Flow cytometric analysis of control and inhibited, swollen cells showed increases in fluorescein isothiocyanate staining and propidium iodide staining in the latter, which are indicative of increases in protein and DNA per cell, respectively. (See FIG. 8). To obtain the data in FIG. 8, the cells were incubated for 24 hours without and with S -(methylthio)-L-homocysteine and copper sulfate as described in regard to FIG. 6. At the end of the incubation, cell number and cell volume distribution (lower panel) were determined and an equal number of cells were removed for staining and analysis as described in the above section entitled Flow Cytometric Analysis. Over $1 \times 10^4$ cells were analyzed and inhibited cells showed a 60% increase in protein, a 35% increase in DNA and a 100% increase in volume. The following legend applies to FIG. 8:

FWD SCR = forward scatter;

90° SCR = 90° scatter of light;

The Abscissa denotes the magnitude of item shown in panel;

The Ordinate denotes the relative number of cells.

The correspondence between protein distribution and 90° scatter with volume distribution of the cells is particularly striking.

Homocysteine And Metal Binding

Cecil and McPhee (See Cecil, R., and McPhee, J. R., "Further Studies On The Reaction Of Disulfides With Silver Nitrate", *Biochem. J.* 66:538-543 (1957)) observed that homocystine reacted with silver ion at a rate 267 times that of cystine and that this increased rate was dependent upon the presence of unsubstituted amino groups. They indicated (See Cecil, P., and McPhee, J. R., "The Sulfur Chemistry Of Proteins", *Adv. Protein Chem.* 14:299-302 (1959)) that the metal ion was bound by ammine formation and therefore brought closer to the disulfide bond. Appropriate configuration required that two methylene groups were spaced between the unsubstituted amino group and the disulfide, possibly to allow hydrogen bond formation in the unsubstituted amino acid. Thus, a similar reaction rate did not occur with cystine. It is noteworthy that SMETH has the same amino to disulfide configuration as homocystine, and that the cuprous ion has nearly identical reactivities as the silver ion (See Cotton, F. A., and Wilkinson, G., *Advanced Inorganic Chemistry.* 4th Edition, John Wiley & Sons, NY, p. 966, (1980)).

Copper - Disulfide Bonding And Reactivity

The coordination between the cuprous ion and a symmetrical disulfide as described by Ottersen, Warner and Seff (Ottersen, T., Warner, L. G., and Seff, K., "Synthesis And Crystal Structure Of A Dimeric Cyclic Copper (I)-aliphatic Disulfide Complex: cyclo-Di-µ-{bis[2-(N,N-dimethylamino)ethyl]disulfide}-dicopper(I) tetrafluoro-borate," *Inorg. Chem.* 13:1904–911 (1974)) involves a lengthening of the disulfide bond and thus its weakening:

The moiety thus becomes a much better leaving group than the original —SR.

The sulfur-sulfur bond becomes more susceptible to nucleophilic attack, and the structure may be considered an example of an intermediate in concomitant electrophilic and nucleophilic catalysis of the scission of this bond as described by Kice (See Kice, J. L., "Electrophilic And Nucleophilic Catalysis Of The Scission Of The Sulfur-Sulfur Bond", *Accts. Chem. Res.* 1:58–64 (1968); Kice, J. L., The Sulfur-sulfur Bond, in *Sulfur in Organic and Inorganic Chemistry* Vol. 1, (A. Senning, ed.). Marcel Dekker, NY, 195,196 (1971)):

Relation To Reaction With The Enzyme Active Site

The positioning of glutamine in CTP synthetase relative to its reactive thiolate anion can be represented diagramatically as indicated by Levitzki (See Levitzki, A., "The allosteric control of CTF Synthetase", in *The Enzymes of Glutamine Metabolism* (See S. Prusiner, and E. R. Stadtman, eds.); Academic Press, NY 505-521 (1973)) in FIG. 9A. In this representation, the glutamine subsequently loses its amide group and reacts to form a thio-ester. A corresponding positioning of copper-SMETH is shown in the FIG. 9B. This positioning is dependent upon the "natural" L configuration of SMETH and places the nucleophilic thiolate ion in close proximity to the sulfonium moiety of the copper disulfide function. In accordance with the reactions described above, the cuprous sulfide of homocysteine would act as the leaving group and the enzyme would be methylthiolated. The possibility that migration of the copper to the sulfur of the methylthio-moiety of SMETH would make the methylthio-moiety the leaving group cannot be ignored.

Comparison With Other Glutamine Amidotransferase Inhibitors

Figure 9A:
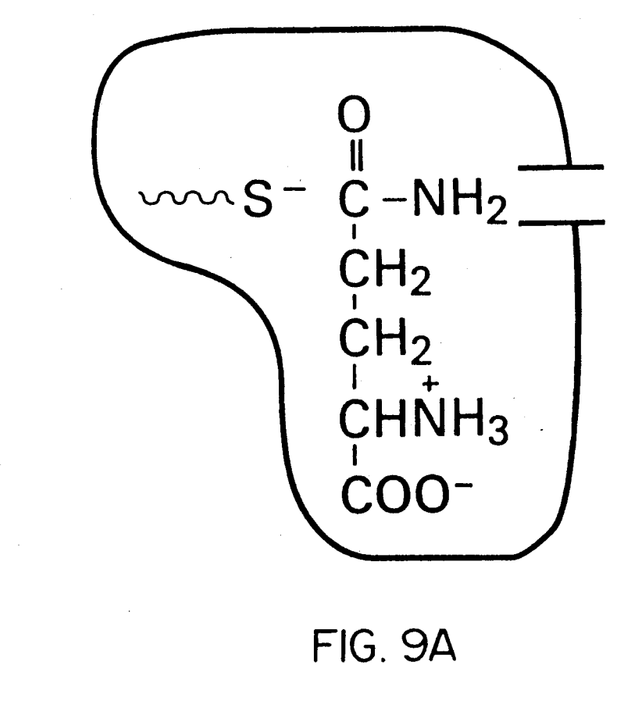
Figure 9B:
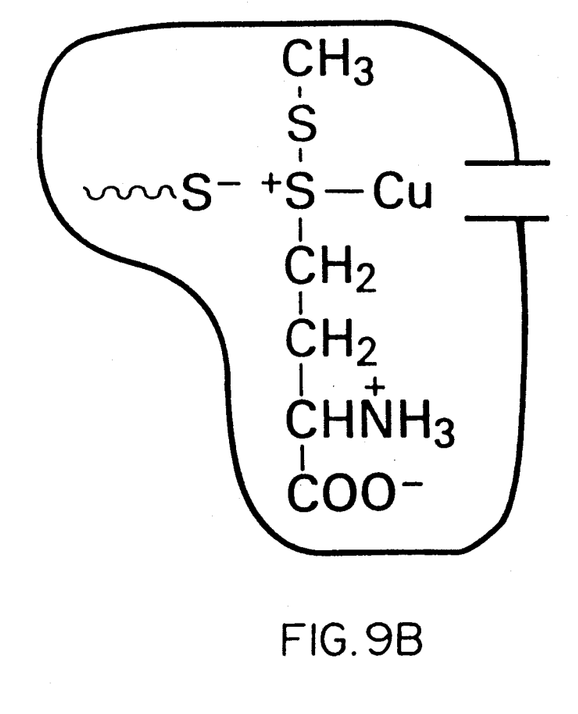

The activity of copper-SMETH differs from that of the natural amido-transferase inhibitors, azaserine, diazo-oxo-norleucine and acivicin in that only one critical cellular pathway is blocked, the amination of UPT to CTP. The other inhibitors also block some sites in purine biosynthesis (See Livingston, R. B., Venditti, J. M., Cooney, D. A., and Carter, S. K., "Glutamine Antagonists In Chemotherapy", *Adv. Pharmacol. Chemotherap.* 8:57-120 (1970)) including the amination step for the synthesis of guanosine monophosphate (See Neil, G. L., Berger, A. E., Bhuyan, B. K., Blowers, C. L., and Kuentzel, S. L., "Studies Of The Biochemical Pharmacology Of The Fermentation-derived Antitumor Agent, (alphaS,5S)-alpha -amino-3-chloro-4,5-dihydro-5-isoxazoleacetizacid (AT-125)", *Adv. Enzyme Regul.* 17:375-398 (1978); and Neil, G. L., Berger, A. E., McPartland, R. P., Grindey, G. B., and Bloch, A. Biochemical And Pharmacological Effects Of The Fermentation-derived antitumor Agent, ($\alpha$S,5S-$\alpha$-amino-3-chloro-4,5-dihydro-5-isoxazoleacetic acid (AT-125). *Cancer Res.* 39:852–865 (1979)). There is currently no explanation for this difference. It should be noted, however, that the reactive center of copper-SMETH is internal (FIG. 9), while in the other glutamine analogs the reactive site may be considered terminal. This introduces the concept of bulk tolerance in inhibitor specificity, for the methylthio- and copper moieties must be acceptable within the reactive site of the enzyme. This factor could be evaluated by determining the potency of copper-SMETH as an inhibitor for the other glutamine amidotransferase. Also, groups larger than methyl can be introduced in the mixed disulfide, to yet further challenge the bulk tolerance of the enzymes from different tissues.

Possible Relationship Between The Biochemical And Cellular Lesions

Homocysteine has been shown to promote endothelial cell damage via copper catalyzed hydrogen peroxide generation (See Starkebaum, G. and Harlan, J. M., "Endothelial Cell Injury Due To Copper -catalyzed Hydrogen Peroxide Generation From Homocysteine", *J. Clin. Invest.* 77:1370–1376 (1986)), to be toxic by blocking methionine metabolism via its adenosyl derivative (See Djurhuus, R., Svardal, A. M., Ueland, P. M., Male, R. and Lillehaug, J. R., "Growth Support And Toxicity Of Homocysteine And Its Effects On Methionine Metabolism In Non-transformed and Chemically Transformed C3H/10T1/2 Cells", *Carcinogenesis* 9:9-16, (1988)) and homocysteine thiolactone may be toxic due to acylations of cellular constituents by the reactive thiolactone moiety (See Dudman, N. P. B. and Wilcken, D. E. L., "Homocysteine Thiolactone And Experimental Homocysteinemia", *Biochem. Med.* 27:244-253 (1982)). Since cells can be protected from SMETH and copper-SMETH inhibitions by glutamine and cytidine, these possible alternative mechanisms of cytotoxicity may be considered inoperative in the present system.

The marked swelling and lysis from the S1ETH and copper-SMETH promoted CTP deficiency may be a consequence <f a block in phospholipid biosynthesis for plasma membrane generation (See Vance, D. E. in *Biochemistry of Lipids and Membranes* (D. E. Vance and J. E. Vance, eds. pp. 242-270 (1985)). This appears probable because the inventors report that DNA and protein synthesis had continued in the inhibited swollen cells and the observation (Ibid.) that the Km of the reactions involving CTP in phospholipid biosynthesis is higher than those of nucleic acid formation. Thus, as the availability of CTP becomes limiting, a block in phospholipid biosynthesis would be the first to become evident, and could result in unbalanced growth, membrane pathology, swelling and lysis.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims:

What is claimed is:

1. An injectable pharmaceutical composition for the treatment of cancers susceptible to treatment therewith, comprising:

(a) an effective amount of S-(methylthio)-DL-homocysteine or the L-enantimorph thereof;
(b) an effective amount of a copper chelate of nitrilotriacetic acid; and
(c) a pharmaceutically acceptable carrier.

2. An injectable pharmaceutical composition for the treatment of cancer susceptible to treatment therewith, comprising:
(a) an effective amount of S-(methylthio)-DL-homocysteine or the L-enantimorph thereof;
(b) an effective amount of a copper chelate of a bis-thiosemicarbazone; and
(c) a pharmaceutically acceptable carrier.

* * * * *